US008846996B2

(12) United States Patent
Kustov et al.

(10) Patent No.: US 8,846,996 B2
(45) Date of Patent: Sep. 30, 2014

(54) SUPPORTED OXIDATIVE DEHYDROGENATION CATALYST

(75) Inventors: Leonid Modestovich Kustov, Moscow (RU); Aleksey Victorovich Kucherov, Moscow (RU); Elena Dmitrievna Finashina, Moscow (RU); Tatyana Nikolaevna Kucherova, Moscow (RU); Vera Ilynichna Isaeva, Moscow (RU); Andrzej Krzywicki, Calgary (CA); Haiyong Cai, Calgary (CA)

(73) Assignee: Nova Chemicals (International) S.A., Fribourg (CH)

( * ) Notice: Subject to any disclaimer, the term of this patent is extended or adjusted under 35 U.S.C. 154(b) by 364 days.

(21) Appl. No.: 13/138,488

(22) PCT Filed: Feb. 22, 2010

(86) PCT No.: PCT/CA2010/000233
§ 371 (c)(1),
(2), (4) Date: Sep. 27, 2011

(87) PCT Pub. No.: WO2010/096909
PCT Pub. Date: Sep. 2, 2010

(65) Prior Publication Data
US 2012/0016171 A1 Jan. 19, 2012

(30) Foreign Application Priority Data
Feb. 26, 2009 (CA) ..................... 2655841

(51) Int. Cl.
*C07C 5/333* (2006.01)
*B01J 23/28* (2006.01)
*B01J 23/00* (2006.01)
*C07C 5/48* (2006.01)
*B01J 35/02* (2006.01)
*B01J 37/00* (2006.01)
*B01J 37/04* (2006.01)
*B01J 27/057* (2006.01)

(52) U.S. Cl.
CPC ........... *B01J 35/023* (2013.01); *C07C 2521/18* (2013.01); *C07C 2521/06* (2013.01); *B01J 23/002* (2013.01); *C07C 5/48* (2013.01); *C07C 2521/10* (2013.01); *C07C 2521/04* (2013.01); *C07C 2523/22* (2013.01); *C07C 2527/057* (2013.01); *C07C 2523/28* (2013.01); *B01J 37/0036* (2013.01); *B01J 2523/00* (2013.01); *B01J 37/04* (2013.01); *B01J 37/0009* (2013.01); *C07C 2523/20* (2013.01); *B01J 27/0576* (2013.01)
USPC ........... 585/662; 502/105; 502/151; 585/658; 585/661; 585/622; 585/663; 241/24.12; 241/24.13

(58) Field of Classification Search
USPC ................ 585/622; 502/105, 151; 241/24.12, 241/24.13
See application file for complete search history.

(56) References Cited

U.S. PATENT DOCUMENTS

| 4,250,346 | A | 2/1981 | Young et al. | |
|---|---|---|---|---|
| 4,450,313 | A | 5/1984 | Eastman et al. | |
| 4,524,236 | A | 6/1985 | McCain | |
| 4,596,787 | A | 6/1986 | Manyik et al. | |
| 4,853,202 | A | 8/1989 | Kuznicki | |
| 4,899,003 | A | 2/1990 | Manyik et al. | |
| 5,808,143 | A * | 9/1998 | Karrer et al. .................. | 562/407 |
| 6,566,573 | B1 | 5/2003 | Bharadwaj et al. | |
| 6,624,116 | B1 | 9/2003 | Bharadwaj et al. | |
| 6,891,075 | B2 | 5/2005 | Liu | |
| 7,319,179 | B2 * | 1/2008 | Lopez Nieto et al. ........ | 585/658 |
| 2010/0222623 | A1 * | 9/2010 | Ryan .............................. | 585/654 |
| 2010/0256432 | A1 * | 10/2010 | Arnold et al. .................. | 585/655 |

FOREIGN PATENT DOCUMENTS

| WO | WO 2005/018804 A1 | 3/2005 |
|---|---|---|
| WO | WO 2005/058498 A1 | 6/2005 |
| WO | PCT/US2006/016458 * | 6/2006 |
| WO | WO 2006/130288 A1 | 12/2006 |

OTHER PUBLICATIONS

Haber, J., Block, J.H., and Delmon, B., Manual of Methods and Procedures for Catalyst Characterization, International Union of Pure and Applied Chemistry, vol. 67, Nos. 8/9, pp. 1257-1306, 1995 IUPAC.*
F. Ivars et al, selective oxidation of short-chain alkanes over hydrothermally prepared MoVTeNbO cat., Topics in Catalysis, vol. 38, Nos. 1-3, Jul. 2006, pp. 59-67.
J.B. Peri et al, The Surface Structure of Silica Gel, J. Phys. Chem., 72 (8) 1968, pp. 2926-2933.

* cited by examiner

*Primary Examiner* — In Suk Bullock
*Assistant Examiner* — Philip Louie
(74) *Attorney, Agent, or Firm* — Kenneth H Johnson

(57) ABSTRACT

The present invention provides a process for the manufacture of an efficient and robust catalyst for the oxidative dehydrogenation of paraffins to olefins, preferably lower $C_{2-4}$ paraffins. The present invention provides a process for the preparation of an oxidative dehydrogenation catalyst of $C_{2-4}$ paraffins to olefins comprising comminuting: from 10 to 99 weight % of a mixed oxide catalyst of the formula $V_xMo_yN-b_zTe_mMe_nO_p$, wherein Me is a metal selected from the group consisting of Ta, Ti, W, Hf, Zr, Sb and mixtures thereof; with from 90 to 1 weight % of an inert matrix selected from oxides of titanium, zirconia, aluminum, magnesium, yttria, lantana, silica and their mixed compositions or a carbon matrix to produce particles having a size from 1 to 100 microns and forming the resulting particles into pellets having a size from 0.1 to 2 mm.

17 Claims, No Drawings

SUPPORTED OXIDATIVE DEHYDROGENATION CATALYST

TECHNICAL FIELD

The present invention relates to a method to prepare an oxidative dehydrogenation catalyst having a high productive and a high hourly space velocity, preferably for the dehydrogenation of ethane to ethylene. In a preferred embodiment the present invention relates to a dry method for the preparation of such a catalyst including the dry comminution of the active catalyst and the support.

BACKGROUND ART

The thermal cracking of paraffins to olefins, particularly lower paraffins such as $C_{2-4}$ paraffins typically ethane and propane to corresponding olefins is an energy intensive process. It has been proposed to catalytically dehydrogenate lower paraffins in the presence of oxygen. Typically a support is impregnated with a liquid catalyst and dried for subsequent use. While these types of catalysts are useful they generally have a low productivity.

Dehydrogenation processes are widely used in modern refining and petrochemistry. Processes of synthesis of butadiene, isoprene, long-chain olefins are commercialized. However, the area of dehydrogenation of light alkanes remains to be underexplored and the processes are far from the commercial scale. The most advanced are the processes of oxidative dehydrogenation based on the use of transition metal oxide catalysts and a robust oxidant, such as oxygen or air. The oxidative conversion makes the process of dehydrogenation thermodynamically advantageous and decreases the reaction temperature as compared to non-oxidative processes (e.g. thermal cracking). The conversion of ethane, which is the second major component of natural gas, to ethylene requires development of new catalysts and processes.

Several catalytic systems are known in the art for the oxidative dehydrogenation of ethane. U.S. Pat. No. 4,450,313, issued May 22, 1984 to Eastman et al., assigned to Phillips Petroleum Company discloses a catalyst of the composition $LiO—TiO_2$, which is characterized by a low ethane conversion not exceeding 10%, in spite of a rather high selectivity to ethylene (92%). The major drawback of this catalyst is the high temperature of the process of oxidative dehydrogenation, which is close to or higher than 650° C.

Rather promising results were obtained for nickel-containing catalysts disclosed in U.S. Pat. No. 6,891,075, 2005 issued May 10, 2005 to Liu assigned to Symyx technologies, Inc. At 325° C. the ethane conversion on the best catalyst in this series was about 20% with a selectivity of 85% (a Ni—Nb—Ta oxide catalyst).

The U.S. Pat. No. 6,624,116, issued Sep. 23, 2003 to Bharadwaj, et al. and U.S. Pat. No. 6,566,573 issued May 20, 2003 to Bharadwaj, et al. both assigned to Dow Global Technologies Inc. disclose Pt—Sn—Sb—Cu—Ag monolith systems that have been tested in an autothermal regime at T>750° C., the starting gas mixture contained hydrogen ($H_2:O_2=2:1$, GHSV=180 000 $h^{-1}$). The catalyst composition is different from that of the present invention and the present invention does not contemplate the use of molecular hydrogen in the feed.

U.S. Pat. No. 4,524,236 issued Jun. 18, 1985 to McCain assigned to Union Carbide Corporation and U.S. Pat. No. 4,899,003, issued Feb. 6, 1990 to Manyik et al, assigned to Union Carbide Chemicals and Plastics Company Inc. disclose mixed metal oxide catalysts of V—Mo—Nb—Sb. At 375-400° C. the ethane conversion reached 70% with the selectivity close to 71-73%. However, these parameters were achieved only at very low gas hourly space velocities less than 900 $H^{-1}$ (i.e. 720 $h^{-1}$). Additionally the supported catalyst is prepared by impregnating the support and not by a dry co-comminution process of the present invention.

The most efficient catalysts were described in the patents by Lopez-Nieto J. M. and coworkers.

U.S. Pat. No. 7,319,179 issued Jan. 15, 2008 to Lopez-Nieto et al. assigned to Consejo Superior de Investigaciones Cientificas and Universidad Politecnica de Valencia, discloses Mo—V—Te—Nb—O oxide catalysts that provided an ethane conversion of 50-70% and selectivity to ethylene up to 95% (at 38% conversion) at 360-400° C. The catalysts have the empirical formula $MoTe_hV_iNb_jA_kO_x$, where A is a fifth modifying element. The catalyst is a calcined mixed oxide (at least of Mo, Te, V and Nb), optionally supported on: (i) silica, alumina and/or titania, preferably silica at 20-70 wt % of the total supported catalyst or (ii) silicon carbide. The supported catalyst is prepared by conventional methods of precipitation from solutions, drying the precipitate then calcining. The patent does not suggest co-communition of the catalyst and a support.

Similar catalysts have been also described in open publications of Lopez-Nieto and co-authors. Selective oxidation of short-chain alkanes over hydrothermally prepared MoVTeNbO catalysts is discussed by F. Ivars, P. Botella, A. Dejoz, J. M. Lopez-Nieto, P. Concepcion, and M. I. Vazquez, in Topics in Catalysis (2006), 38 (1-3), 59-67.

MoVTe—Nb oxide catalysts have been prepared by a hydrothermal method and tested in the selective oxidation of propane to acrylic acid and in the oxidative dehydrogenation of ethane to ethylene. The influence of the concentration of oxalate anions in the hydrothermal gel has been studied for two series of catalysts, Nb-free and Nb-containing, respectively. Results show that the development of an active and selective active orthorhombic phase ($Te_2M_{20}O_{57}$, M=Mo, V, Nb) requires an oxalate/Mo molar ratio of 0.4-0.6 in the synthesis gel in both types of samples. The presence of Nb favors a higher catalytic activity in both ethane and propane oxidation and a better production of acrylic acid. Preparation of molybdenum-vanadium-tellurium-niobium catalyst useful in oxidation involves drying a slurry of a ceramic inert carrier and metal ionic precursor species; then precalcination and calcination of the slurry. This art does not suggest co-comminuting the catalyst and the carrier.

The preparation of a Mo—Te—V—Nb composition is described in WO 2005058498 A1, published 30 Jun. 2005 (corresponding to U.S. published application 2007149390A1). Preparation of the catalyst involves preparing a slurry by combining an inert ceramic carrier with at least one solution comprising ionic species of Mo, V, Te, and Nb, drying the slurry to obtain a particulate product, precalcining the dried product at 150-350° C. in an oxygen containing atmosphere and calcining the dried product at 350-750° C. under inert atmosphere. The catalyst prepared exhibits the activity and selectivity in the oxidation reaction comparable to the non-supported catalyst. Again this teaches away from the co-comminution of the catalyst and the support.

Mixed metal oxide supported catalyst composition; catalyst manufacture and use in ethane oxidation are described in Patent WO 2005018804 A1, 3 Mar. 2005, assigned to BP Chemicals Limited, UK. A catalyst composition for the oxidation of ethane to ethylene and acetic acid comprises (i) a support and (ii) in combination with O, the elements Mo, V and Nb, optionally W and a component Z, which is ≥1 metals of Group 14. Thus, $Mo_{60.5}V_{32}Nb_{7.5}O_x$ on silica was modified with 0.33 g-atom ratio Sn for ethane oxidation with good ethylene/acetic acid selectivity and product ratio 1:1.

A process for preparation of ethylene from gaseous feed comprising ethane and oxygen involving contacting the feed with a mixed oxide catalyst containing vanadium, molybdenum, tantalum and tellurium in a reactor to form effluent of ethylene is disclosed in WO 2006130288 A1, 7 Dec. 2006, assigned to Celanese Int. Corp. The catalyst has a selectivity for ethylene of 50-80% thereby allowing oxidation of ethane to produce ethylene and acetic acid with high selectivity. The catalyst has the formula $Mo_1V_{0.3}Ta_{0.1}Te_{0.3}O_z$. The catalyst is optionally supported on a support selected from porous silicon dioxide, ignited silicon dioxide, kieselguhr, silica gel, porous and nonporous aluminum oxide, titanium dioxide, zirconium dioxide, thorium dioxide, lanthanum oxide, magnesium oxide, calcium oxide, barium oxide, tin oxide, cerium dioxide, zinc oxide, boron oxide, boron nitride, boron carbide, boron phosphate, zirconium phosphate, aluminum silicate, silicon nitride, silicon carbide, and glass, carbon, carbon-fiber, activated carbon, metal-oxide or metal networks and corresponding monoliths; or is encapsulated in a material (preferably silicon dioxide ($SiO_2$), phosphorus pentoxide ($P_2O_5$), magnesium oxide (MgO), chromium trioxide ($Cr_2O_3$), titanium oxide ($TiO_2$), zirconium oxide ($ZrO_2$) or alumina ($Al_2O_3$). However, the methods of preparation of the supported compositions involve the procedures of wet chemistry (solutions are impregnated into the solid support and then the materials are dried and calcined).

The preparation of a supported catalyst usable for low temperature oxy-dehydrogenation of ethane to ethylene is disclosed in the U.S. Pat. No. 4,596,787 A, 24 Jun. 1986 assigned to UNION CARBIDE CORP. A supported catalyst for the low temperature gas phase oxydehydrogenation of ethane to ethylene is prepared by (a) preparing a precursor solution having soluble and insoluble portions of metal compounds; (b) separating the soluble portion; (c) impregnating a catalyst support with the soluble portion and (d) activating the impregnated support to obtain the catalyst. The calcined catalyst has the composition $Mo_aV_bNb_cSb_dX_e$. X is nothing or Li, Sc, Na, Be, Mg, Ca, Sr, Ba, Ti, Zr, Hf, Y, Ta, Cr, Fe, Co, Ni, Ce, La, Zn, Cd, Hg, Al, Tl, Pb, As, Bi, Te, U, Mn and/or W; a is 0.5-0.9, b is 0.1-0.4, c is 0.001-0.2, d is 0.001-0.1, e is 0.001-0.1 when X is an element. The patent fails to teach or suggest a co-comminution of the catalyst and the support.

Another example of the low temperature oxy-dehydrogenation of ethane to ethylene using a calcined oxide catalyst containing molybdenum, vanadium, niobium and antimony is described in the U.S. Pat. No. 4,524,236 A, 18 Jun. 1985 and U.S. Pat. No. 4,250,346 A, 10 Feb. 1981, both assigned to UNION CARBIDE CORP. The calcined catalyst contains $Mo_aV_bNb_cSb_dX_e$ in the form of oxides. The catalyst is prepared from a solution of soluble compounds and/or complexes and/or compounds of each of the metals. The dried catalyst is calcined by heating at 220-550° C. in air or oxygen. The catalyst precursor solutions may be supported on to a support, e.g. silica, aluminum oxide, silicon carbide, zirconia, titania or mixtures of these. The selectivity to ethylene may be greater than 65% for a 50% conversion of ethane.

The trend in the prior art is the formation of a catalyst by impregnating a porous support and then calcining. The resulting catalysts tend to have a fairly low times space yield.

The present invention seeks to provide a method of preparation of a supported active catalyst for oxidative dehydrogenation of ethane into ethylene that would exhibit a superior performance (activity, selectivity and productivity) as compared with the systems described in the prior art. The novel composite catalyst comprises the Mo—V—Nb—Te—O oxide composition containing the known in the art M1 phase and a solid support with the surface area in the range of 1-100 m²/g. The support may be silica, alumina, titania, zirconia, ceria, lanthana, magnesia, zinc oxide or a mixture thereof. The active composite catalyst is prepared by co-comminution of a mixture of the active Mo—V—Nb—Te—O oxide catalyst and a support so that the weight percent of the active phase is ranging from 10 to 99%. The resulting fine powder with the particle size ranging from 1 to 100 microns can be then pressed into pellets and crushed to collect the necessary fraction ranging from 0.1 to 1-2 mm or extrudates can be formed that can be further loaded in the plug-flow catalytic reactor.

DISCLOSURE OF INVENTION

The present invention provides a process for the preparation of an oxidative dehydrogenation catalyst of $C_{2-4}$ paraffins to olefins comprising comminuting:
a) from 10 to 99 weight % of a mixed oxide catalyst of the formula $V_xMo_yNb_zTe_mMe_nO_p$, wherein Me is a metal selected from the group consisting of Ta, Ti, W, Hf, Zr, Sb and mixtures thereof; and:
x is from 0.1 to 3;
y is from 0.5 to 1.5;
z is from 0.001 to 3;
m is from 0.001 to 5;
n is from 0.001 to 2;
and p is a number to satisfy the valence state of the mixed oxide catalyst; with:
b) 90 to 1 weight % of an inert matrix selected from oxides of titanium, zirconia, aluminum, magnesium, yttria, lantana, silica and their mixed compositions or a carbon matrix;
to produce particles having a size from 1 to 100 microns and forming the resulting particles into pellets having a size form 0.1 to 2 mm.

The present invention also provides the catalyst prepared by the above method and a process for the oxidative dehydrogenation of lower ($C_{2-4}$) alkanes to the corresponding alkene.

BEST MODE FOR CARRYING OUT THE INVENTION

In the catalyst of the present invention the mixed metal oxide is used in an amount from 10 to 99, preferably from 30 to 80, most preferably from 40 to 70 weight % of the total catalyst and the support is present in an amount from 90 to 1, preferably from 70 to 20, most preferably from 60 to 30 weight % of the total catalyst.

The mixed metal oxide has the formula:

$$V_xMo_yNb_zTe_mMe_nO_p,$$

wherein Me is a metal selected from the group consisting of Ta, Ti, W, Hf, Zr, Sb and mixtures thereof; and
x is from 0.1 to 3, preferably from 0.2 to 2;
y is from 0.5 to 1.5, preferably from 0.95 to 1.05, most preferably 1;
z is from 0.001 to 3, preferably from 0.001 to 2, most preferably from 0.01 to 1.5;
m is from 0.001 to 5, preferably from 0.2 to 2;
n is from 0.001 to 2, preferably from 0.001 to 1, most preferably from 0.01 to 0.8;
and p is a number to satisfy the valence state of the mixed oxide catalyst.

In the above formula the numbers represent the molar amounts of the components. Preferably the ratio of x:m is from 0.3 to 10, most preferably from 0.5 to 8, desirably from 0.5 to 6.

The active metal catalyst may be prepared by mixing aqueous solutions of soluble metal compounds such as hydroxides, sulphates, nitrates, halides lower ($C_{1-5}$) mono or di carboxylic acids, and ammonium salts or the metal acid per se. For instance, the catalyst could be prepared by blending solutions such as ammonium metavanadate, niobium oxalate, ammonium molybdate, telluric acid etc. The resulting solution is then dried typically in air at 100-150° C. and calcined in a flow of inert gas such as those selected from the group consisting of $N_2$, He, Ar, Ne and mixtures thereof at 200-600° C., preferably at 300-500° C. The calcining step may take from 1 to 20, typically from 5 to 15 usually about 10 hours. The resulting oxide is a friable solid.

The support for the catalyst selected form oxides of titanium, zirconia zirconium, aluminum, magnesium, yttrium, lanthanum, silicon and their mixed compositions or a carbon matrix. The support should have a large surface area typically greater than about 100 $m^2/g$, preferably greater than about 200 $m^2/g$, most preferably from 250 $m^2/g$ to 1,000 $m^2/g$. The support will be porous and will have a pore volume from about 0.3 to 5.0 ml/g, typically from 0.5 to 3.0 ml/g.

It is also believed titanium silicates such as those disclosed in U.S. Pat. No. 4,853,202 issued Aug. 1, 1989 to Kuznicki assigned to Engelhard Corporation would be useful as supports in accordance with the present invention.

It is important that the support be dried prior to use. Generally, the support may be heated at a temperature of at least 200° C. for up to 24 hours, typically at a temperature from 500° C. to 800° C. for about 2 to 20 hours, preferably 4 to 10 hours. The resulting support will be free of adsorbed water and should have a surface hydroxyl content from about 0.1 to 5 mmol/g of support, preferably from 0.5 to 3 mmol/g.

The amount of the hydroxyl groups in silica may be determined according to the method disclosed by J. B. Peri and A. L. Hensley, Jr., in *J. Phys. Chem.*, 72 (8), 2926, 1968, the entire contents of which are incorporated herein by reference.

The support and catalyst may be combined and then comminuted to produce a fine particulate material having a particle size ranging from 1 to 100 micron. The communition process may be any conventional process including ball and bead mills, both rotary, stirred and vibratory, bar or tube mills, hammer mills, and grinding discs. A preferred method of comminution is a ball or bead mill.

In one embodiment of the invention the catalyst and the support are dry milled. It is also possible to wet mill the catalyst and support provided the resulting product is again dried and if necessary calcined.

The particulate material may be sieved if required to select the appropriate small particle size. The particulates may then be compacted and crushed to yield particles having a size from 0.1 to 1-2 mm. The particles or extrudates can be formed that can be further loaded in the plug-flow catalytic reactor.

The oxidative dehydrogenation reaction will typically be conducted at temperatures from 300° C. to 600° C., preferably from 400° C. to 600° C. and pressures from 15 to 50 psig (103.4 to 344.73 kPag). The molar ratio of oxygen to feed typically ranges from 1:2.5 to 1:10, preferably from 1:2.5 to 1:3.5. The gas hourly space velocity (GHSV) will be from 900 to 18000 $h^{-1}$, preferably greater than 1000 $h^{-1}$. The space-time yield of alkene (e.g. ethylene) (productivity) in g/hour per Kg of catalyst should be not less than 300 preferably greater than 500, most preferably greater than 950, most desirably greater than 1,000 at 380° C. It should be noted that the productivity of the catalyst will increase with increasing temperature.

While the present invention is primarily directed to the manufacture of alkenes from the corresponding alkane it may also be possible to convert the feed to carboxylic acids.

The present invention will now be illustrated by the following non limiting examples.

EXAMPLES

Example 1

Preparation of the Active Oxide Catalyst Phase No Support 2.65 g of ammonium heptamolybdate (tetrahydrate) and 0.575 g of telluric acid were dissolved in 19.5 g of distilled water at 80° C. Ammonium hydroxide (25% aqueous solution) is added to the Mo- and Te-containing solution at a pH of 7.5. Then water is evaporated under stirring at 80° C. The solid precipitate is dried at 90° C. 3.0 g of this precipitate is suspended in water (21.3 g) at 80° C. and 0.9 g of vanadyl sulfate and 1.039 g of niobium oxalate were added. The mixture was stirred for 10 min and then is transferred to the autoclave with a Teflon® (tetrafluoroethylene) lining. Air in the autoclave was substituted with argon, the autoclave was pressurized and heated to 175° C. and the system was kept for 60 hours at this temperature. Then the solid formed in the autoclave was filtered, washed with distilled water and dried at 80° C. The thus obtained active catalyst phase was calcined at 600° C. (2 h) in a flow of argon. The temperature was ramped from room temperature to 600° C. at 1.67° C./min. The powder was pressed then and the required mesh size particles were collected.

The catalyst was tested in oxidative dehydrogenation of ethane using a gas mixture $O_2/C_2H_6$ with the ratio from 1/2.5 to 1/10, preferably from 1/2.5 to 1/3.5. The mixture was fed in the plug-flow reactor with the gas hourly space velocity of 900-18000 $h^{-1}$ at a pressure of 1-10 atm, preferably at 1 atm.

The catalysts were tested at 320-450° C., the catalyst loading 0.13-1.3 g; fraction 0.25-0.5 mm, a flow type reactor with a stationary catalyst bed was used. The catalyst was heated to 360° C. in the reaction mixture (15-75 cc/min), the catalytic activity was measured at 380, 420, and 450° C. The data for all the catalysts are presented in the table.

Example 2

Preparation of the Supported Composite Catalyst

The active catalyst phase prepared in Example 1 and alpha-alumina with the specific surface area 10 $m^2/g$ were mixed and placed in the ball mill, the percentage (weight) of $\alpha$-$Al_2O_3$ in the mixture was 50 wt %. The ball milling was carried out at room temperature for 30 min. until a fine powder with an average particle size of 3.5 micron was obtained. The obtained milled powder is pressed into pellets, crushed and the fraction having a size of 0.25-0.5 mm is collected. The obtained catalytic composite material was tested in oxidative dehydrogenation of ethane under conditions of Example 1 (see the table).

Example 3

Preparation of the Supported Mo—V—Te—Nb—O Mixed Oxide Catalyst by the Wet Method 6.400 g Ammonium telluromolybdate [$(NH_4)_6TeMo_6O_{24}$ 7$H_2O$] was dissolved into 20 ml of distilled water (first solution). An aqueous solution of $VOSO_4$ was prepared by dissolving 2.370 g of hydrated $VOSO_4$ in 10 ml of distilled water (second solution). A third solution was prepared by dissolving 2.330 g hydrated niobium oxalate in 10 ml distilled water heated at 353 K. The second solution was then added to the first solution and the resulting mixture was stirred for 5 min. The third solution was finally added to the mixed solution together with α-$Al_2O_3$ and the resulting slurry was stirred for 10 min and then transferred to an autoclave. After 5 min of nitrogen purging, hydrothermal reaction was carried out for 48 h at 448K. The obtained powder was washed with distilled water, dried at 353 K overnight and then calcined under nitrogen flow at 873 K for 2 h. The catalyst was tested as in Example 1. The date is given in the table.

Example 4

Preparation of Titania-Based Composite Material

This sample was prepared according to Example 2 except for the use of $TiO_2$ as a carrier instead of α-$Al_2O_3$. 50% wt of $TiO_2$ (surface area 25 m$^2$/g) was used.

TABLE 1

Catalytic Performance of the Bulk and Supported Catalysts in Oxidative Dehydrogenation of Ethane

| Catalyst (Example) | T, ° C. | Space-time yield of ethylene (productivity), g/h per 1 kg of catalyst | Selectivity, % |
|---|---|---|---|
| 1 (bulk sample, comparative) | 400 | 210 | 90-92 |
| 2 (composite catalyst with 50% α-$Al_2O_3$) | 380 | 980 | 96.5 |
|  | 420 | 2300 | 96 |
| 3 (supported catalyst prepared from solutions, comparative) | 380 | 270 | 92 |
|  | 420 | 520 | 91 |
| 4 (composite catalyst with 50% $TiO_2$) | 380 | 1200 | 97.5 |
|  | 420 | 2500 | 97 |

It is seen from this comparison that, first, the catalysts prepared according to the invention are more active than the best catalysts known in the art, and second, the catalysts prepared by ball milling of the most active mixed oxide catalyst with an appropriate support show a dramatic enhancement of the specific activity (activity per 1 g of the active phase) as compared with the bulk catalysts.

INDUSTRIAL APPLICABILITY

The present invention provides a novel catalyst for the oxidative dehydrogenation of paraffins, particularly lower $C_{2-4}$ paraffins, to the corresponding olefin, preferably α-olefin.

The invention claimed is:

1. A process for the preparation of an oxidative dehydrogenation catalyst of ethane to ethylene comprising co-comminuting:
   a) from 10 to 99 weight % of a mixed oxide catalyst of the formula
   $V_xMo_yNb_zTe_mMe_nO_p$, wherein Me is a metal selected from the group consisting of
   Ti, W, Hf, Zr and mixtures thereof; and
   x is from 0.1 to 3;
   y is from 0.5 to 1.5;
   z is from 0.001 to 3;
   m is from 0.001 to 5;
   n is from 0.001 to 2 and p is a number to satisfy the valence state of the mixed oxide catalyst;

with:
   b) 90 to 1 weight % of an inert matrix selected from oxides of titanium, zirconium, aluminum, magnesium, yttrium, lanthanum, silicon and their mixed compositions or a carbon matrix, to produce particles having a size from 1 to 100 microns and forming the resulting particles into pellets having a size form 0.1 to 2 mm.

2. The process according to claim 1 wherein the oxidative dehydrogenation catalyst has an ethylene selectivity of at least 96 weight % and has a productivity of not less than 300 g of olefin per 1 kg of the catalyst active phase per hour at a temperature from 300° C. to 600° C., a pressure from 1 to 10 atmospheres, and a gas hourly space velocity from 900 to 1800 h$^{-1}$.

3. The process according to claim 2 wherein component a, is present in an amount from 30 to 80 weight %.

4. The process according to claim 3, wherein in component a, y is from 0.95 to 1.05.

5. The process according to claim 4, wherein in component a, x and m are from 0.02 to 2.

6. The process according to claim 5, wherein in component a, z is from 0.001 to 0.5.

7. The process according to claim 6, wherein in component a, n is from 0.001 and 1.

8. The process according to claim 7, wherein in the comminuting process is ball milling.

9. The process according to claim 7, wherein component a is prepared by mixing components in a liquid phase to produce a product and subsequently drying the product to form component a and wherein the process comprises dry mixing and dry ball milling components a and b.

10. The process according to claim 9, wherein component b is titania.

11. The process according to claim 8, wherein component b is magnesia.

12. The process according to claim 8, wherein component b is carbon or graphitized carbon.

13. The process according to claim 8, wherein component b is alumina.

14. A process for the oxidative dehydrogenation of ethane to ethylene comprising contacting a feed comprising ethane and oxygen with a catalyst at a gas hourly space velocity from 900 to 1800 h$^{-1}$, at a temperature from 300 C to 600 C, at a pressure from 15 to 50 psig (103.4 to 344.73 kPag), and a molar ratio of oxygen to feed from 1:2.5 to 1:10, wherein the catalyst has a productivity of not less than 300 g of olefin per 1 kg of the catalyst active phase per hour and an ethylene selectivity of at least 96 weight % and wherein a process for preparing the catalyst comprises co-comminuting a mixture consisting of:

a) from 10 to 99 weight % of a mixed oxide catalyst of the formula $V_xMo_yNb_zTe_mMe_nO_p$, wherein Me is a metal selected from the group consisting of Ti, W, Hf, Zr and mixtures thereof; and x is from 0.1 to 3;
y is from 0.5 to 1.5;
z is from 0.001 to 3;
m is from 0.001 to 5;
n is from 0.001 to 2;

and p is a number to satisfy the valence state of the mixed oxide catalyst;
and
b) 90 to 1 weight % of an inert matrix selected from oxides of titanium, zirconium, aluminum, magnesium, yttrium, lanthanum, silicon and their mixed compositions or a carbon matrix;
to produce particles having a size from 1 to 100 microns and forming the resulting particles into pellets having a size from 0.1 to 2 mm.

15. The process according to claim 14, wherein the productivity of the catalyst exceeds 1000 g of olefin per 1 kg of the catalyst active phase per hour.

16. The process according to claim 15, having a gas hourly space velocity greater than 900 $h^{-1}$.

17. An oxidative dehydrogenation catalyst prepared by the process according to claim 1.

* * * * *